United States Patent [19]
Muszak et al.

[11] Patent Number: 5,330,625
[45] Date of Patent: Jul. 19, 1994

[54] ROUND POTENTIOMETRIC SLIDE ELEMENTS AND METHOD OF USING THE SAME

[75] Inventors: Martin F. Muszak; Thomas R. Kissel, both of Rochester; Maurice A. Kildal, Webster, all of N.Y.

[73] Assignee: Eastman Kodak Company, Rochester, N.Y.

[21] Appl. No.: 965,824

[22] Filed: Oct. 23, 1992

[51] Int. Cl.⁵ .................................. G01N 27/333
[52] U.S. Cl. ........................... 204/153.1; 204/400; 204/416
[58] Field of Search ............. 204/153.1, 400, 403, 204/416, 418, 419

[56] References Cited

U.S. PATENT DOCUMENTS

| | | | |
|---|---|---|---|
| 4,123,701 | 10/1978 | Josefsen et al. | 324/448 |
| 4,184,936 | 1/1980 | Paul et al. | 204/400 |
| 4,273,639 | 6/1981 | Gottermeier | 204/416 |
| 4,517,071 | 5/1985 | Seshimoto | 204/419 |
| 4,627,906 | 12/1986 | Gough | 204/418 |
| 4,654,127 | 3/1987 | Baker et al. | 204/416 |
| 5,126,034 | 6/1992 | Carter et al. | 204/431 |
| 5,192,415 | 3/1993 | Yoshioka et al. | 204/416 |

FOREIGN PATENT DOCUMENTS 59-70956  4/1984  Japan .

Primary Examiner—T. Tung
Attorney, Agent, or Firm—Dana M. Schmidt

[57] ABSTRACT

There are disclosed an ISE slide element and potentiometric measurement of assaying, using a slide element that is positionally insensitive about an axis of symmetry. This is achieved by accessing one of the electrodes in the center of the slide element, and the other in an annular groove centered on the element center, both for liquid contact and electrometer contact. Preferably, electrometer contact occurs at a side of the electrode opposite to the side contacted with liquid.

11 Claims, 2 Drawing Sheets

ROUND POTENTIOMETRIC SLIDE ELEMENTS AND METHOD OF USING THE SAME

FIELD OF THE INVENTION

This invention relates to a slide element and method for doing potentiometric assays using paired ion-selective electrodes.

BACKGROUND OF THE INVENTION

Potentiometric slide elements for so-called "dry assays" are well-known, and are described, for example, in U.S. Pat. Nos. 4,184,936 and 4,273,639. Such known elements feature a pair of identical ion-selective-electrodes, hereinafter "ISE's", coupled together with an ion bridge that is generally fibrous in nature. One of the two ISE's is contacted with patient sample liquid, and the other with a reference fluid. The ISE's function to provide a differential charge, depending on the relative ionic concentrations of the analyte, for a differential analysis. The ISE's are exposed at opposite surfaces, so that their ion-selective membranes are exposed to the sample liquid or reference liquid, and their metal layers are exposed to the contacts of an electrometer.

Because of the format of the ISE's and the connecting bridge, the overall slide element has been rectangular in configuration. Although such a configuration has worked well, it is constraining in that it does not lend itself to, e.g., a circular configuration. Indeed, prior to this invention it has been difficult to provide a circular potentiometric slide element using paired ISE's and a connecting ion bridge, precisely because such ISE's and a bridge have not been so configurable.

Circular potentiometric slide elements, on the other hand, become essential if future analyzers are to be converted to slide elements that are circular for all assays (both colorimetric and potentiometric). Unlike those using rectangular frames, slide elements constructed from round frames have no special orientation in an analyzer. This is both a benefit and a possible hindrance. The benefit is that the slide elements can be rotated into any particular station without regard to any particular orientation of a side edge. The possible hindrance is that if there is any feature of the slide element that lacks axial symmetry, it is difficult to position a round slide element to take that asymmetry into account.

Colorimetric slide elements easily lend themselves to a round format; potentiometric elements do not.

Yet another disadvantage of the rectangular ISE slide elements is that the sample deposit must occur off-center. This is contrary to the center depositing of sample that occurs for colorimetric slide elements, necessitating therefore a complicated alteration of the dispenser tip location when the type of slide element changes. For ease in dispensing, it is preferred that all sample dispensing occur at the center of the slide element.

SUMMARY OF THE INVENTION

I have constructed a potentiometric slide element wherein the ISE's and the ion bridge connecting them are conducive to making the slide have a round configuration. That is, by providing a central ISE, a concentric ISE about the central ISE, and ion bridges extending from the central ISE, the outer slide is oriented about a polar axis of symmetry. Such orientation invites a circular configuration.

More specifically, in accord with one aspect of the invention there is provided a potentiometric slide element, comprising a first, generally centrally disposed ion-selective-electrode, a second ion-selective-electrode identical in chemical composition to the first, but shaped as an annulus, a frame for mounting and electrically isolating the electrodes with the second electrode generally centered on and surrounding the first electrode and with both electrodes being exposed on opposite sides, and at least one ion bridge between the electrodes extending from the central ion-selective electrode to the annulus of the second electrode, so that the slide element is symmetric about an axis extending through the first electrode.

In accord with another aspect of the invention, there is provided a potentiometric slide element for differential ion activity analysis, the element comprising two substantially identical ion-selective electrodes insulatively spaced from each other, at least one ion bridge between the electrodes, and a frame holding the electrodes and bridge. The element is improved in that the frame is generally round when viewed in plan, the electrodes are spaced apart along the radii of the round frame each with a continuous circumference, and the bridge extends radially between the electrodes, whereby the electrodes can be disposed to impart axial symmetry to the slide element.

In accord with still another aspect of the invention, there is provided a method of analyzing a sample liquid using a potentiometric slide element, comprising the steps of a) dispensing one of a sample liquid and a reference liquid onto an ISE in a central location of a slide element constructed with identical ISE's in said central location and in an annular groove spaced away from and centered on said central location a known distance, the slide element having an ion bridge portion fluidly connecting the central location with the annular groove, b) dispensing the other of the liquids into any portion of the annular groove so that the liquid contacts the ISE in the annular groove, c) allowing a differential ionic activity to develop in said electrodes, and an ionic bridge to form in the bridge portion, and d) contacting the ISE's with an electrometer, so that said slide element can be used regardless of its axial orientation about said central location.

Accordingly, it is an advantageous feature of the invention that a potentiometric slide can be provided in round format, which because of its axis of symmetry, is independent of any preferred orientation about that axis. Hence, such a round ISE slide can be handled in an analyzer like any round slide element, that is, without concern regarding its orientation about that axis.

It is a related advantageous feature that such a slide element can be metered with liquid, and detected with a potentiometer, simply by applying liquid or a potentiometer to the central portion and to any part of a circumference known to be the desired distance from the central portion where the other electrode is located, without regard to where along the circumference that this occurs.

Yet another related advantageous feature of the invention is that sample is dispensed onto the center of the slide element, whether that element is a colorimetric element or a potentiometric element, avoiding the need to alter the position of the dispensing tip.

Other advantageous features will become apparent upon reference to the following Detailed Description when read in light of the attached drawings.

DESCRIPTION OF THE PREFERRED EMBODIMENTS

The following description is of the preferred embodiments, wherein the two electrodes have a preferred layered construction and are mounted in a frame of a preferred construction. Additionally, any type of ion-selective electrode useful in differential analysis, and any other frame construction, are useful in the invention, provided that the slide element has axial symmetry and the electrodes are left exposed for contact with liquid and an electrometer.

Figure 1:
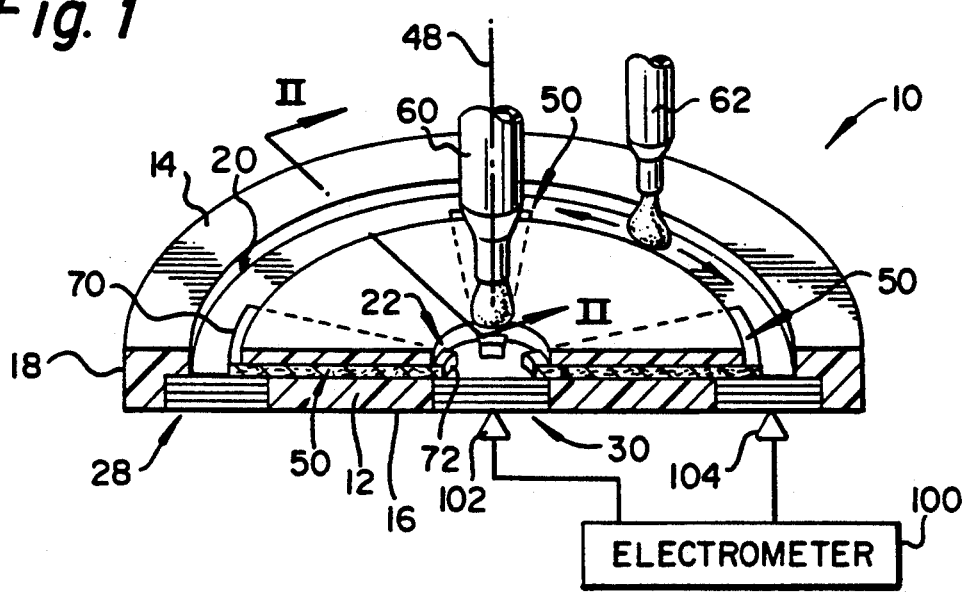
FIG. 1 is an isometric view, taken in section, of one half of a potentiometric slide element of the invention.

As is conventional with most ISE slide elements, the slide element 10 of the invention comprises a frame 12, FIG. 1, two substantially identical (except for shape) ISE's 28 and 30, and one or more, preferably more, ion bridges 50 extending between the two ISE's. As used herein, an "ion bridge" is a linkage between two ISE's which is insulative unless and until a liquid containing ions wets the bridge to establish an ionic bridge between the liquids.

Regarding the frame 12, it comprises an upper surface 14, a lower surface 16, and an exterior sidewall 18 which is preferably in the invention in the shape of a cylindrical section, to give element 10 a round shape when viewed in plan. Surface 14 is apertured at 20 and 22, FIG. 2, to provide liquid access to ISE's 28 and 30, respectively, while surface 16 is apertured at 24, 26 so as to hold ISE's 28 and 30 with a metallic face 42 exposed for selective contact by electrometer 100, FIG. 1. Such apertures are conventional except conventionally they appear in one surface only, and not in opposite surfaces. The depth of the apertures can be varied. A preferred form of apertures 20 and 22 is one that is deeper than the height of the liquid deposited therein.

The electrodes themselves are preferably constructed so as to be layered, in the manner taught in, e.g., U.S. Pat. Nos. 4,273,639 and 4,214,968, with the exceptions noted hereinafter. That is, conventionally each of the electrodes comprises the following 5 contiguous layers: a plastic support layer 32, FIG. 3, on top of which is a layer 34 of a metal such as silver. Above that is a layer 36 of an insoluble metal salt, such as AgCl. Above that is a layer 38 of a reference electrolyte, and finally, as one exposed side of the electrode, a layer 40 of an ion-selective membrane. The chemistries of these layers is identical for each of the electrodes 28 and 30, preferably by punching them out from the same small rectangle of a coated sheet, to ensure identical matched behavior in the two electrodes.

In accordance with one aspect of the invention, the exceptions to the conventional electrode construction are as follows (for both electrodes): the support layer 32, FIG. 3, must be electrically conductive from both of its sides, as is apparent from the electrometer contact at 102 and 104 shown in FIG. 1. As shown, layer 32 can be a conventional 0.3 mm thick plastic, as shown, with apertures 44 therethrough coated as is conventional at 34 with silver, and at 42 with a layer of meltable conductive plastic melted to fill apertures 44. Still further (not shown), layers 32 and 42 can be combined into a single conductive plastic layer (e.g., containing carbon or metal particles for conduction). Yet another alternative (not shown) is to replace layers 32 and 42 with a conductive metal layer, e.g., copper.

It is this construction which allows opposite exposed sides of the electrode to be accessed for contact by the liquid, and the electrometer, rather than the same exposed side as with conventional electrodes. In turn, it is the accessing of opposite sides that reduces the size that slide element needs to have, as will become apparent.

In accordance with another aspect of the invention, the shape and location of the electrodes are modified as follows:

Electrode 30 is a round button of small diameter, e.g., about 2-10 mm, and comprises a control electrode mounted in aperture 26, both the electrode and aperture 26 being generally centrally located in frame 12, most preferably centered on axis 48 of the element. That is, although the centering of electrode 30 on axis 48, the center axis of symmetry of element 10, will ensure that the electrode is centered for dispensing liquid thereon, the electrode can be slightly off-center from axis 48 and still function well.

Electrode 28 however is an annulus, shaped to surround electrode 30 and to be spaced a known insulative distance from electrode 30. Preferably, it is centered on the center of electrode 30, for example, by being centered on axis 48. However, it can be off-center from axis 48, provided aperture 20 of the frame is properly constructed. Because electrode 28 is a complete annulus, its circumference is continuous, i.e., unbroken, thereby ensuring axial symmetry to the slide element. (Electrode 30 trivially provides a continuous circumference due to its round shape).

Apertures 20, 22, 24 and 26 are other aspects of the invention. Clearly, aperture 26 will control the location of central electrode 30, as noted above. Most preferably, aperture 22 is concentric with aperture 26, to ensure proper drop deposition. Similarly, apertures 24 and 20, control the positioning of electrode 28 and its access to liquid. For that reason, apertures 20 and 24 are also annular. Most importantly, aperture 20 should be centered on aperture 22, and most preferably, both apertures 20 and 22 are centered on axis 48. The centering of apertures 20 and 22 on axis 48 ensures that proper dispensing will occur simply by locating one dispenser 60, FIG. 1, on the center axis 48 of the element and another dispenser 62 anywhere on the circumference of the known radius r, FIG. 2, the distance to the middle of aperture 20, regardless of how much rotation element 10 has experienced about axis 48. "r" can be, e.g., about 8 mm. That is, the two electrodes are positionally insensitive due to their apertures being centered on the axis of symmetry. On the other hand, electrode 28 can be slightly off-center, since aperture 20 covers some of exposed side 40, and thus covers that portion that might be off-center.

The electrodes are sealed in apertures 26 and 28, such as by adhesives, to prevent liquid from leaking around the exposed edges of the electrodes, as is known in the art.

The remaining essential component of element 10 is ion bridge 50, FIG. 1. That bridge can have any conventional construction, such as a fibrous material, e.g., the paper construction described in capillary bridge 44 of U.S. Pat. No. 4,273,639. If bridge 50 is fibrous, it preferably comprises segments, which can be wedge-shaped, disposed generally on radii of the element (radiating from axis 48), so as to extend between the two electrodes. Most preferably, the wedges do not extend the full circumference, to minimize the amount of liquid needed to form the ionic bridge within the ion bridge. Thus, FIG. 2, there are circumferential segments 66 around axis 48 that have only insulative plastic of frame 12 between the two electrodes. The number of segments that this leaves for the bridges can be varied, but at least three such segments are used, each spanning an arc of about 10° to 30°, for example 20°, of the circle around axis 48, FIG. 1. Less than three can mean an unacceptable length of time required to wet a bridge from aperture 20 and form an ionic junction in the bridge. Thus, four or five are preferred. More than six tends to increase too much the fibrous volume that has to be wetted.

The amount of the arc filled in by each bridge segment is a function of variability in fluid flow therethrough, induced by the fact that the drop from tip 62, FIG. 1, can be either right in a bridge segment, or in between (as the 2 extremes). Thus, the angular extent of the bridge segments is adjusted to ensure that the two deposited liquids always meet somewhere between ends 70 and 72, regardless of where tip 62 ends up being located vis-a-vis segments 50. This in turn is controlled by the relative fluid volumes and the height of segments 50, as will be apparent. Still further, the bridge segments 50 need not be perfectly pie-shaped, as shown, but can be bowed outward as needed to ensure a liquid-liquid junction forms between, and not at, ends 70 and 72.

When in fibrous form, bridges 50 may have their ends 70 extending out into aperture 20, FIG. 1, to increase their wettability. Care is needed if this is done also with ends 72 in aperture 22, as too much extension of the ends can prevent the liquid from contacting electrode 30.

Optionally (not shown), the portion of frame 12 overlying bridges 50 can be vented along a radial line above the bridge to allow escape of air entrapped by liquid advancing in the bridge.

It is not essential that bridges 50 rest upon the electrodes at the ends of the bridges. Instead, they can be raised above the electrode surface.

The opposite apertures 24 and 26 expose metal side 42 of the electrode.

The use of the slide element 10 will be readily apparent from the preceding description. Briefly, FIG. 1, element 10 is used with apertures 20 and 22 facing up, and is placed at a metering station at which dispensing tips 60 and 62 are located. Its rotational orientation about axis 48 and the central location of electrode 30 is irrelevant, due to its axial symmetry. A sample liquid is dispensed by either tip 60 or 62, into either aperture 22 or 20, respectively, and a conventional reference liquid is dispensed by the other tip into the other aperture, either simultaneously or at a slightly different time. As will be apparent, much more liquid is needed for aperture 20 than for aperture 22, e.g., about 50–100 μL compared to 1–10 μL. Therefore, preferably the reference fluid is used in aperture 20. Still further, because wetting of end 70 will take longer to occur in aperture 20 than the wetting of end 72 in aperture 22, in some situations tip 62 dispenses shortly before the dispensing from tip 60, so that bridges 50 will wet at least ends 70 with liquid from tip 62, before any bridge entirely fills up with the liquid from tip 60. Exactly how much delay is preferred, if any, between the two dispensing steps will depend on the void volume to be filled in the bridges, and the number of bridge segments 50 that are used, as will be readily apparent.

Figure 2:
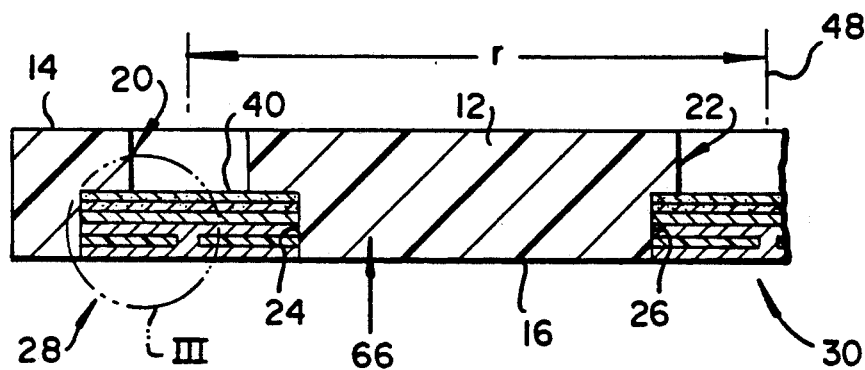
FIG. 2 is a section view taken generally along the line II—II of FIG. 1, illustrating the non-bridging portion of the frame.

The dispensing by tip 62 can occur at any place within aperture 20, at the distance "r" from axis 48, FIG. 2.

Thus the needed ionic junction between the two liquids will form inside bridges 50, and a differential ionic activity will develop in the electrodes 28 and 30.

Figure 3:
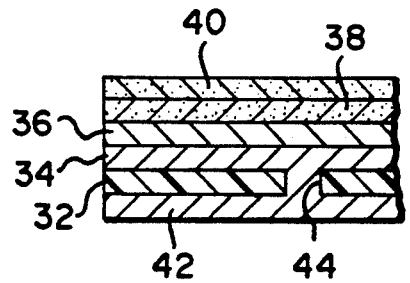
FIG. 3 is an enlarged section view of the circled portion of FIG. 2 marked "III"

Thereafter, probes 102 and 104 of electrometer 100 are brought to bear against metallic sides 42 of each electrode, FIG. 3. This is achieved by simply bringing probe 102 into contact at axis 48, FIG. 1, and probe 104 spaced the predetermined radial distance r from axis 48, FIG. 2, anywhere along the annular electrode 28. Slide element 10 thus has positional insensitivity about axis 48.

The advantage of having probes 102 and 104 contact the slide elements from the side opposite to the side contacted with liquid is primarily that the presence of the ion bridges 50 along certain, but not all, radii extending along side 40 from axis 48, render it practically impossible to bring the probes down onto that same side 40 with positional insensitivity. That is, even if the electrode were constructed to extend layer 34 out beyond the edges of the layers 36, 38 and 40 above it, so as to be contactable through a suitable aperture from above (the same side), the possibility of a bridge 50 being in the way, particularly as regards electrode 30, prevents the electrodes from being operative anywhere around the axis at the desired radial distance from axis 48. This in turn destroys positional insensitivity.

Figure 4:
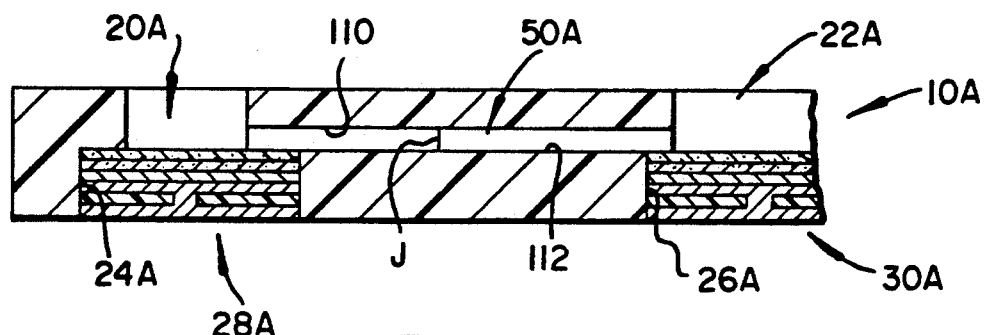
FIG. 4 is a section view similar to that of FIG. 2, but taken along the bridging portion of the frame and illustrating an alternate bridge construction.

It is not necessary that the ion bridge be a paper bridge. It can alternatively be a capillary transport bridge, FIG. 4, as taught for example in U.S. Pat. No. 4,302,313. Parts similar to those previously described bear the same reference numeral to which the distinguishing suffix "A" has been appended.

Thus, element 10A has apertures 20A, 22A, 24A, 26A and electrodes 28A and 30A as described in the previous embodiment. However, the spaced-apart ion bridges 50A are radial passageways that are capillary transport zones, instead of fibrous wedges, such zones being constructed for capillary transport of the two liquids to form a junction within the zone, e.g., at junction "J". As is known from previous publications, opposing surfaces 110 and 112 of zone 50A are constructed and spaced so as to provide such capillary transport. They can be with or without surface texturing and/or coatings, as is already known for such layers.

Alternatively, the bridges 50A need not be straight-line radial paths, but can be any set of paths (not shown) connecting the two electrodes.

The arc occupied by bridges 50A around axis 48 can be the same percentage as would otherwise be the case if bridges 50A were fibrous segments as described above.

Because the outside apertures 20 and 24 in the above embodiments are completely exposed to both liquid and electrometer around their entire circumference, the electrode 28 or 28 A has to provide a significant part of the strength of the slide test element. However, it is not essential in all cases that this be done to establish positional insensitivity of the slide element. Instead, FIGS. 5 and 6, the frame of the slide element can have spokes extending out across aperture 20B, as explained hereinafter, to reinforce the strength of the frame. Parts similar to those previously described bear the same reference numeral to which the distinguishing suffix "B" is appended.

Figure 5:
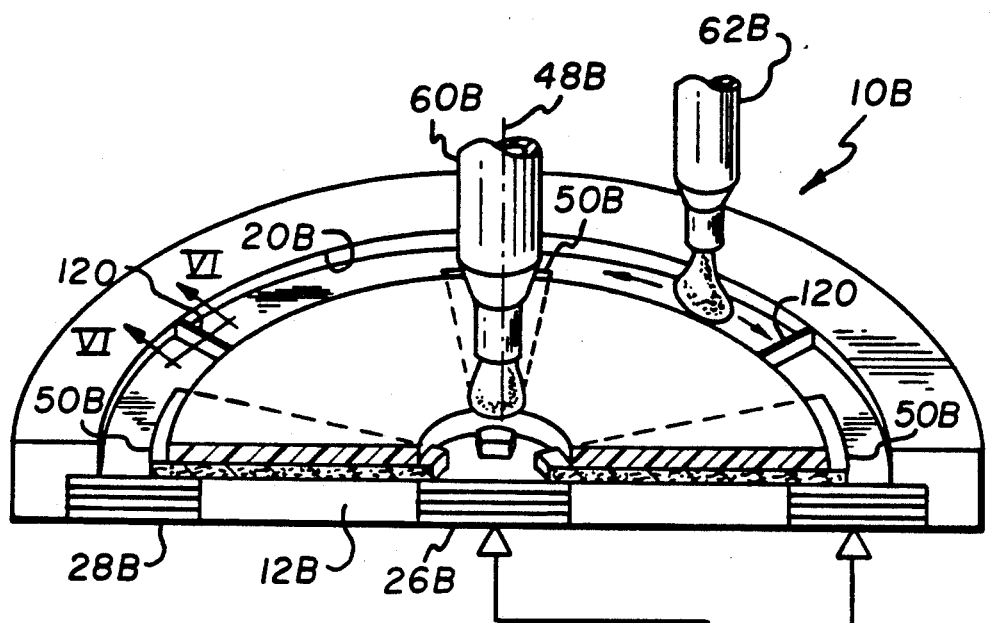
FIG. 5 is a view similar to that of FIG. 1 but of an alternate embodiment.

More specifically, there is included as part of frame 12B in slide element 10B, a spoke 120 that connects the frame across electrode 28B, there being a spoke in between each bridge segment 50B, FIG. 5. However, to ensure that liquid deposited by tip 62B does NOT sit on top of a spoke, if the tip ends up directly above a spoke for dispensing, the spoke is tapered to a knife edge at 122 at the outer surface of the spoke, FIG. 6. As a result, IF liquid is dropped on the spoke, it simply splits up and flows down into aperture 20B, arrows 124 and 126. Thus the operative symmetry of the slide element about axis 48B, FIG. 5, is not destroyed.

Spokes 120 have an additional advantage: they break up the amount of liquid needed in aperture 20B into 1/nth the amount otherwise needed, where "n" is the number of spokes present. Since a bridge segment is automatically included between 2 spokes, the liquid supplied by tip 62B, FIG. 5, need be only the amount needed to partially wet the ONE bridge segment involved between the 2 operative spokes that confine the liquid deposited, until the junction is formed with the liquid deposited by tip 60B.

Figure 6:
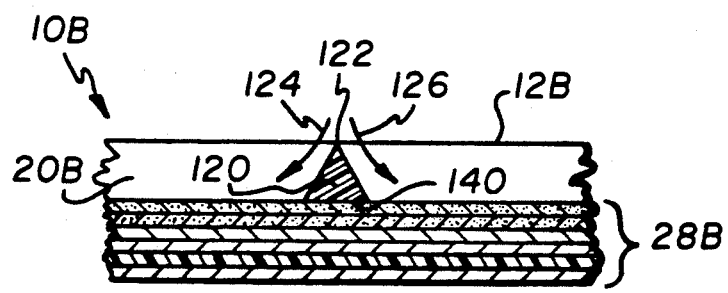
FIG. 6 is a section view taken generally along the line VI—VI of FIG. 5.

The adhesive or sealing means used in apertures 26B and 28B, FIG. 5, to keep liquid from leaking around the edges of the electrodes, is preferably also used underneath spokes 120, at area 140, FIG. 6, to keep the liquid from spreading into adjacent portions of aperture 20B.

The invention disclosed herein may be practiced in the absence of any element which is not specifically disclosed herein.

The invention has been described in detail with particular reference to preferred embodiments thereof, but it will be understood that variations and modifications can be effected within the spirit and scope of the invention.

What is claimed is:

1. A potentiometric slide element, comprising a first, generally centrally disposed ion-selective-electrode,
    a second ion-selective-electrode identical in chemical composition to said first, but shaped as an annulus,
    a frame for mounting and electrically isolating said electrodes with said second electrode generally centered on and surrounding said first electrode and with both said electrodes being exposed on opposite sides,
    and at least one ion bridge between said electrodes extending from said central ion-selective electrode to said annulus of said second electrode along a radius from said first electrode,
    so that the slide element is symmetric about an axis extending through said first electrode.

2. A potentiometric slide element, comprising a first, generally centrally disposed ion-selective-electrode,
    a second ion-selective-electrode identical in chemical composition to said first, but shaped as an annulus,
    a frame for mounting and electrically isolating said electrodes with said second electrode generally centered on and surrounding said first electrode and with both said electrodes being exposed on opposite sides,
    and at least one ion bridge between said electrodes extending from said central ion-selective electrode to said annulus of said second electrode,
    so that the slide element is symmetric about an axis extending through said first electrode, said frame further including a spoke for each of said at least one bridge, extending across a surface of the outermost of said electrodes, each of said spokes including surface means for directing liquid deposited on the spoke, into contact with said outermost electrode.

3. A slide element as defined in claims 1 or 2, wherein said ion bridge comprises a fibrous material.

4. A slide element as defined in claims 1 or 2, wherein said ion bridge comprises a capillary transport passageway within said frame.

5. A slide element as defined in claims 1 or 2, wherein said electrodes each comprise a plastic support with a conductive layer on both of the opposite sides of said support, so that said electrodes can be contacted with an electrometer from the side opposite to the side which is contacted with liquid.

6. A slide element as defined in claims 2, wherein said surface means comprise a knife edge at the outer surface of said spoke.

7. A method of analyzing a sample liquid using a potentiometric slide element, comprising the steps of
    a) dispensing one of a sample liquid and a reference liquid onto an ion-selective electrode in a central location of a slide element an annularly-shaped ion-selective electrode in an annular groove spaced away from and centered on said central location a known distance, said electrodes being of substantially identical composition, the slide element also having an ion bridge portion fluidly connecting said central location with said annular groove;
    b) dispensing the other of the liquids into any portion of said annular groove so that the liquid contacts the ion-selective electrode in said annular groove;
    c) allowing a differential ionic activity to develop in said electrode, and an ionic bridge to form in said bridge portion; and
    d) contacting the ion-selective electrodes with an electrometer, so that said slide element can be used regardless of its rotational orientation about said central location.

8. A method of analyzing as defined in claim 7, wherein step b) occurs prior to step a).

9. In a potentiometric slide element for differential ion activity analysis, the element comprising two substantially identical ion-selective electrodes insulatively spaced from each other, at least one ion bridge between the electrodes, and a frame holding said electrodes and bridge;
    the improvement wherein said frame is generally round when viewed in plan, said electrodes are spaced apart along the radii of said round frame, each with a continuous circumference, and said bridge extends radially between said electrodes,
    whereby said electrodes can be disposed to impart axial symmetry to the slide element.

10. In a potentiometric slide element for differential ion activity analysis, the element comprising two ion-selective electrodes substantially identical in composition and insulatively spaced from each other, at least one ion bridge between the electrodes, and a frame holding said electrodes and bridge;

the improvement wherein said frame is generally round when viewed in plan, said electrodes are spaced apart along the radii of said round frame, each with a continuous circumference, and said bridge extends radially between said electrodes, whereby said electrodes can be disposed to impart axial symmetry to the slide element, said frame further including a spoke for each of said at least one bridge, extending across a surface of the outermost of said electrodes, each of said spokes including surface means for directing liquid deposited on the spoke, into contact with said outermost electrode.

11. A slide element as defined in claim 10, wherein said surface means comprise a knife edge at the outer surface of said spoke.

* * * * *